United States Patent [19]
Burov et al.

[11] Patent Number: 5,672,707
[45] Date of Patent: Sep. 30, 1997

[54] 9-AMINOACRIDINE DERIVATIVES POSSESSING PSYCHOTROPIC, ANTIAMNESTIC AND LIPID-REGULATIVE ACTIVITY

[75] Inventors: Yury Valentinovich Burov, Moscow; Sergei Borisovich Goncharenko, Moskovskaya oblast; Tatyana Nikolaevna Robakidze, Moskovskaya oblast; Jury Nikolaevich Portnov, Moskovskaya oblast; Ljubov Vladislavovna Kadysheva, Moskovskaya oblast, all of Russian Federation; Ilmar Kharievich Penke, Riga, Latvia; Eduard Maximovich Peganov, Moscow, Russian Federation; Svetlana Alexeevna Sukhanova, Moskovskaya oblast, Russian Federation; Galina Vasilievna Tananova, Moscow, Russian Federation; Anatoly Evgenievich Voronin, Moskovskaya oblast, Russian Federation; Anatoly Alexeevich Kotlobai, Moskovskaya oblast, Russian Federation; Yanis Fritsevich Oshis, Riga, Latvia; Lidia Evgenievna Pchelintseva, Moskovskaya oblast, Russian Federation

[73] Assignee: Vserossiisky Nauchny Tsentr Po Bezopasnosti Biologicheski Aktivnykh veschestv (Vntsbav), Moskovskaya, Russian Federation

[21] Appl. No.: 145,330

[22] Filed: Oct. 29, 1993

Related U.S. Application Data

[63] Continuation of Ser. No. 211,127, filed as PCT/RU92/00096, May 6, 1992, abandoned.

[30] Foreign Application Priority Data

May 7, 1991 [RU] Russian Federation .......... 4941883/04

[51] Int. Cl.$^6$ ..................... A61K 31/435; C07D 219/10
[52] U.S. Cl. ................................ 546/105; 546/106
[58] Field of Search ..................... 546/105, 106

[56] References Cited

U.S. PATENT DOCUMENTS

| | | | |
|---|---|---|---|
| 4,735,953 | 4/1988 | Lauretskaya et al. | 514/313 |
| 4,839,364 | 6/1989 | Schutske et al. | 546/105 |
| 5,053,513 | 10/1991 | Lee et al. | |

FOREIGN PATENT DOCUMENTS

| | | | |
|---|---|---|---|
| 0179383 | 4/1986 | European Pat. Off. | 546/105 |
| 0371388 | 6/1990 | European Pat. Off. | 546/105 |
| 92/19598 | 11/1992 | WIPO | 546/105 |

OTHER PUBLICATIONS

Bielavsky, Coll. Czech. Chem. Commun vol. 42 pp. 2802–2808 (1977).

*Primary Examiner*—Donald G. Daus
*Attorney, Agent, or Firm*—Ladas & Parry

[57] ABSTRACT

"Derivatives of 9-aminoacridine characterized by psychothropic, antiamnestic and lipid-regulating activities".

New chemical compounds derived of 9-aminoacridine with a general formula are presented:

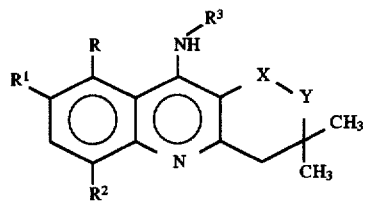

where R=H or $CH_3$ $R^1$=H, $CH_3$, or Br $R^2$=H, $CH_3$ $R^3$=—$C_1$–$C_5$ alkyl phenylmethyl, substituted phenylmethyl or diethylaminoethyl X=C=O, or CHOH, Y=$CH_2$ or

X+Y=CH=CH and their salts with organic and inorganic acids.

The target compounds were obtained by a reaction of substituted nitriles of anthranilic acid with dimedone and subsequent cyclization of intermediate enaminonitriles to the corresponding 9-amino-3,4-dihydroacridine-1(2H)-ones. The reduction of the compounds or their alkylated or aralkylated at 9-aminogroupe derivatives results in corresponding alkanols, which on dehydratation give 9-amino-3,4-dihydroacridines.

In animal experiments the derivatives of 9-aminoacridine in question showed psychothropic, antiamnestic and lipid-regulating activities and less toxicity as compared with known reference drugs.

1 Claim, No Drawings

9-AMINOACRIDINE DERIVATIVES POSSESSING PSYCHOTROPIC, ANTIAMNESTIC AND LIPID-REGULATIVE ACTIVITY

This application is a continuation of Ser. No. 08/211,127 filed Jan. 7, 1993 now abandoned which is a 371 of PCT/RU92/00096 filed May 6, 1992.

TECHNICAL FIELD

The development refers to new chemical compounds, particularly to the derivatives of 9-aminoacridine, which show psychotropic, antiamnestic and lipid-regulative activity and may be used in medical practice to treat psychic diseases, in particular senile dementia of Alzheimer's type, as well as diseases connected with disturbances of lipid metabolism.

PRIOR ART

The drug tactine (Summers W. K. et all.//New Engl. J. med. 1986, Vol. 315, No. 20, p. 1241) is widely used abroad in Alzheimer's disease clinics; a new original drug amiridine has been developed at National Research Center for Biologically Active Compounds (USSR Patent Application N 4076765 from 01.07.86. A61K 31/47; U.S. Pat. No. 4,735,953, cl. 514,313, 1988; BRD Patent N 3231571, A 61K 31/47,1988).

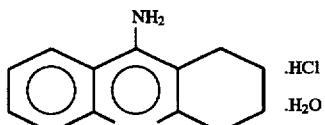

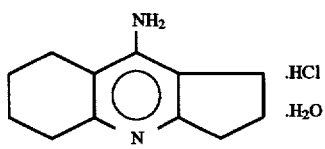

The drawbacks of the above drugs are their comparatively high toxicity, side effects of cholinergic nature (tremor, diarrhea, salivation), and toxic effect of tactine on liver.

Derivatives of 9-aminoacridines having a general formula

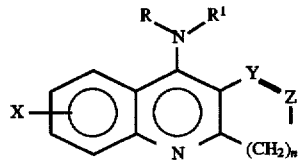

with a structure similar to that of claimed compounds and possessing psychotropic and memory stimulative activity are known (European Patent Application N 0179383 C07D 219/10, -1985; Shutske G. M. et al.//J. Med. Chem. -1989, 32, 1805–1813; Shutske G. M. et al.//J. Med. Chem. -1988, 31, 1279–1282).

Shortcoming of these compounds is a comparatively high toxicity and as a consequence of this—a low therapeutic index.

Structure analogues of the claimed compounds having a formula are known (European Patent Application N 0371388, C07D 219/10, -1990)

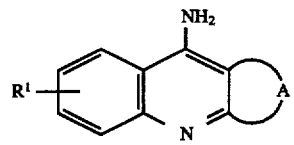

where $\bigcirc$ A is

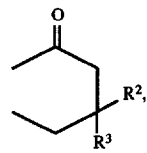

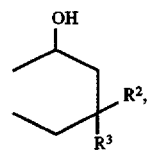

which are inhibitors of acetylcholinesterase; however, there is no information on their antiamnestic and lipid-regulative activity.

DETAILED DESCRIPTION OF THE INVENTION

Derivatives of 9-aminoacridine represented by the formula

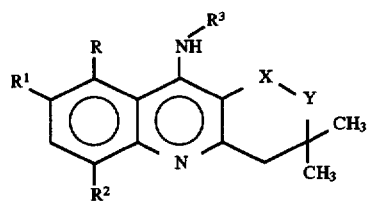

where R=H or CH

R1=H,CH3 or Br

R2=H or CH3

R3=$C_1$-$C_5$ alkyl, arylmethyl or, diethylaminoethyl

X=C=O or CHOH

Y=$CH_2$ or

X+Y=CH=CH and their pharmaceutically acceptable acid addition salts are disclosed.

The preparation of the compounds is performed following the scheme

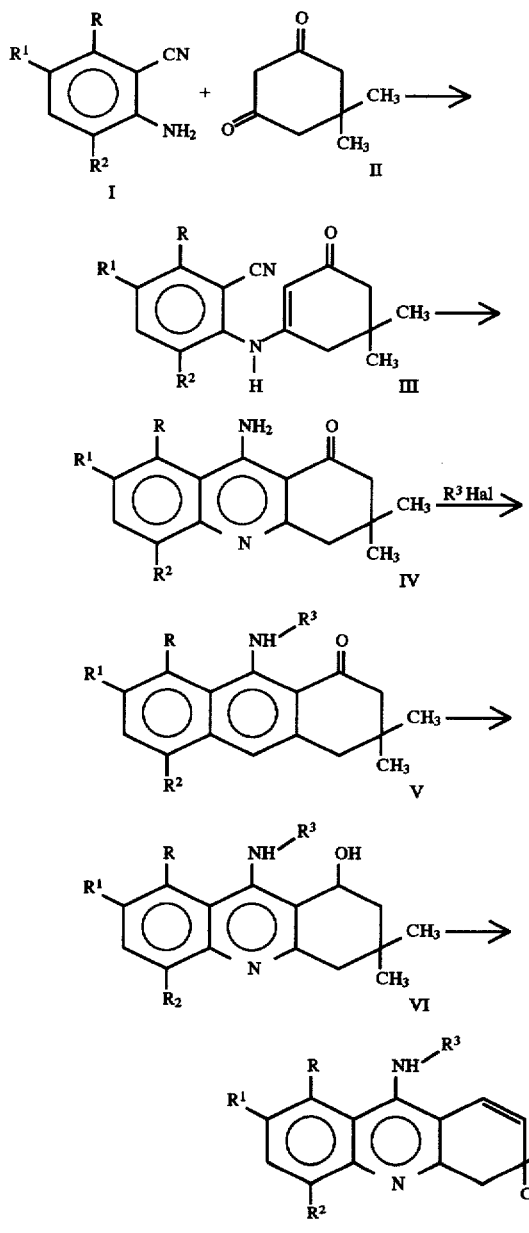

The compounds having the formula V–VII are prepared by interaction of the corresponding substituted nitrile of aminoanthranilic acid I with dimedone II and subsequent cyclization of the hydrochloride of the substituted 2-[(5,5-dimethyl-5-oxocyclohex-1-enyl) amino] benzonitrile III thus obtained into substituted 9-amino-3,3-dimethyl-3,4-dihydroacridine-1(2H)-ones IV; alkylation of compounds IV with aryl- or arylalkylhalogenides into 9-alkyl(arylakyl)-amino-3,3-dimethyl-3,4-dihydroacridine-1(2H)-ones V; reduction of the compounds IV and V into 9-alkyl(arylalkyl) amino-3,3-dimethyl-1,2,3,4-tetrahydroacridine-1-ols VI; dehydratation of the compounds VI into 9-alkyl(arylalkyl) amino-3,3-dimethyl-3,4-dihydroacridines VII.

The invention is illustrated with following examples.

EXAMPLE 1

2-[5,5-dimethyl-3-oxocyclohex-1-enyl)amino] benzonitrile hydrochloride (IIIa)

6 ml of concentrated hydrochloric acid were added to a solution of 4.72 g (0.04 mol) of anthrsnilonitrile (Ia) in 80 ml of THF with stirring, after 15 min 5.6 g (0.04 mol) of dimedone (II) were added, the mixture was heated under reflux with stirring for 12 h, the precipitate was filtered off, washed with acetone and dried. The mother liquor was concentrated to ⅓ of the initial volume, the precipitate was filtered off, washed with acetone and dried. Precipitates were combined to give 9.1 g (82%) of IIIa, m.p. 214–215 (i-PrOH).

EXAMPLE 2

2-[(5,5-dimethyl-3-oxocyclohex-1-enyl)amino]-3,6-dimethyl-benzonitrile hydrochloride (IIId)

6 ml of concentrated hydrochloric acid were added to a solution of 5.84 g (0.04 mol) of 3,6-dimethylanthranilonitrile (Ib) in 80 ml of THF with stirring, after 15 min 5.6 g (0.04 mol) of dimedone (II) were added, the mixture was heated under reflux with stirring for 14 h, the precipitate was filtered off, washed with acetone and dried. The mother liquor was concentrated to ¼ of the initial volume, the precipitate was filtered off, washed with acetone and dried. Precipitates were combined to give 10.5 g (87%) of IIId, m.p. 208–209 (i-PrOH).

Compounds IIIc-g (Table 1) were prepared in an analogous manner.

EXAMPLE 3

9-amino-3,3-dimethyl-3,4-dihydroacridine-1(2H )-one (IVa)

To a Suspension of 27.7 g (0.1 mol) of enamine hydrochloride IIIa in 200 ml of dry THF 27.6 g (0.2 mol) of $K_2O_3$ powder and 0.5 g CuCl were added, the mixture was heated under reflux with stirring for 5 h, the hot solution was filtered, the precipitate on the filter was washed with water and dried- Organic mother liquor was evaporated to ⅕ of the original volume, the precipitate was filtered off, washed with water, dried and combined with the former precipitate. Recrystallization from aqueous EtOH gave 21.4 g (89%) of IVa, m.p. 223–224.

EXAMPLE 4

9-amino-3,3-dimethyl-3,4-dihydroacridine-1(2H)-one (IVa)

To a suspension of 27.7 g (0.1 mol) of enamine hydrochloride IIIa in 300 ml of dry dioxane 27.6 g (0.2 mol) of $K_2CO_3$ powder and 0.5 g CuBr were added, the mixture was heated under reflux with stirring for 5 h, the precipitate was filtered off, washed with water and dried. Organic mother liquor was evaporated to ⅕ of the original volume, the precipitate was filtered off, washed with water, dried and combined with the former precipitate. Recrystallization from aqueous EtOH gave 21.8 g (91%) of IVa, m.p. 223–224.

Compounds IVc-1 (Table 2) were prepared in an analogous manner.

EXAMPLE 5

9-benzylamino-3,3-dimethyl-3,4-dihydroacridine-1(2H)-one (Va).

To a solution of 4.8 g (0.02 mol) of the amine IVa in 70 ml of dry DMSO 2.8 g (0.05 mol) of KOH powder were added, the mixture was stirred for 1 h, then 0.8–1 ml of benzyl chloride was added, the solution was allowed to stand overnight, then poured into 350 ml of water, stirred for 0.5 h, left to stand for a day, the precipitate was filtered off, washed with water, dried and recrystallized from aqueous EtOH to give 5.8 g (88%) of Va, m.p. 169–170.

Compounds Vb-3-(Table 2) were prepared in an analogous manner.

EXAMPLE 6

9-benzylamino-3,3-dimethyl-3,4-dihydro acridine-1(2H)-one (Va).

The mixture of 2.4 g (0.01 mol) of the amine IVa, 1.4 g (0.011 mol, 1.27 ml) of benzyl chloride, 0.5 g of $Bu_4NB_r$, 75 ml of CH2Cl2 and 50 ml of 50% aqueous NaOH was vigorously stirred for 20 h, then poured into 200 ml of ice water, an organic phase was separated, the aqueous phase was extracted with chloroform, (4×50 ml), combined extracts were evaporated, the residue was recrystallized from aqueous EtOH to give 5.8 g (88%) of Va, m.p. 169–170.

Compounds Vo (Table 2) were prepared in an analogous manner.

EXAMPLE 7

9-benzylamino-3,3-dimethyl-1,2,3,4-tetrahydroacridine-1-ol (VIe).

To a suspension of 3.3 g (0.01 mol) of a in 80 ml of absolute THF 0.42 g (0.011 mol) of lithium aluminium hydride was added at 0–5, the mixture was stirred for 2 h under nitrogen current at the same temperature, au excess of lithium aluminium hydride was decomposed by subsequent adding of saturated solution of ammonoum chloride and 30% aqueous potassium hydroxide. An organic phase was separated, the solvent was evaporated, the residue was recrystallized from aqueous EtOH to give 3.2 g (96%) of VIe, m.p. 175–176.

Compounds VIa-d,f-j (Table 3) were prepared in an analogous manner.

EXAMPLE 8

9-benzylamino-3,3-dimethyl-3,4-dihydroacridine-1(2H)-one hydrochloride (VIIe).

The solution of 3.32 g (0.01 mol) of VIe in a mixture of 40 ml of EtOH and 5 ml of concentrated HCl was heated under reflux for 1 h. The solvent was evaporated, the residue was recrystallized from aqueous EtOH to give 3.36 g (98%) of VIIe, m.p. 236–237.

Compounds VIIa-d (Table 4) were prepared in an analogous manner

Psychoneurotropic activity of the declared compounds and their influence on learning and memory were observed using unbred male (18–20 g) mice and 180–200 g) rats, held at standard conditions (room temperature 21°–22° C., 12-hours lighting schedule, food and water ad libitum).

All the compounds in question underwent the following tests:

Acute toxicity was studied by the method of Kerber with intra peritoneal drug injection.

Psychotropic activity test included the influence of drugs on animal behavior, motor activity, on the effects of hexenal (30 and 60 mg/kg), arecoline 925 mg/kg, and apomorphine (2 mg/kg). The drugs were applied intraperitoneally in the dose of 1/20 of LD. 6 mice were in the each experimental group.

Step-down test was used to study the influence of drugs on learning and memory in mice using the model of amnesia achieved by the injection of the central ACh-receptors inhibitor scopolamine (Sc).

TABLE 1

2-[(5,5-Dimethyl-3oxocyclohex-1-enyl)amino]benzonitriles III

| W | | | | | M.p. | IR spectrum | Found, % | | | |
|---|---|---|---|---|---|---|---|---|---|---|
| n/n 1 | R 2 | $R^1$ 3 | $R^2$ 4 | HX 5 | °C. 6 | v, $sm^{-1}$ 7 | C 8 | H 9 | N 10 | Cl 11 |
| Wa | H | H | H | HCl | 214–215 | 2800–2400,2230 1680,1575,1550 1480 | 65,10 | 6,40 | 9,68 | 12,76 |
| WB | H | H | H | — | 187–188 | 3230,3150,3090, 3060,3030,2230 1590,1570,1520 1475 | 74,57 | 6,94 | 11,70 | |
| Wc | H | Br | H | HCl | >250 | 2800–2400,2230 1600,1550,1515 | 50,23 | 4,80 | 7,37 | 9,89 |
| Wd | $CH_3$ | H | $CH_3$ | HCl | 208–209 | 3150,2800–2400 2220,1605,1570, 1530 | 67,36 | 7,16 | 9,2 | 11,42 |
| We | H | $CH_3$ | $CH_3$ | HCl | 239–241 | 2800–2400,2220 1600,1530,1515 | 67,42 | 7,11 | 8,67 | 11,49 |
| Wf | H | $CH_3$ | H | HCl | 209–210 | 2800–2400,2220 1595,1560 | 65,77 | 6,62 | 9,78 | 11,90 |
| Wg | H | H | $CH_3$ | HCl | 207–208 | 3130,2800–2400 | 66,29 | 6,62 | 9,71 | 11,72 |

| | Calculated, % | | | | reaction time, | Yield, |
|---|---|---|---|---|---|---|
| Empirical Formula 12 | C 13 | H 14 | N 15 | Cl 16 | h 17 | % 18 |
| $C_{15}H_{16}N_2O.HCl$ | 65,10 | 6.19 | 10,12 | 12,81 | 2 | 93 |

TABLE 1-continued

2-[(5,5-Dimethyl-3-oxocyclohex-1-enyl)amino]benzonitriles III

| | | | | | | |
|---|---|---|---|---|---|---|
| $C_{15}H_{16}N_2O$ | 74,97 | 6,71 | 11,66 | | | |
| $C_{15}H_{15}BrN_2O.HCl$ | 50,66 | 4,54 | 7,88 | 9,97 | 5 | 87 |
| $C_{17}H_{20}N_2O.HCl$ | 66,99 | 6,95 | 9,19 | 11,63 | 14 | 87 |
| $C_{17}H_{20}N_2O.HCl$ | 66,99 | 6,95 | 9,19 | 11,63 | 14 | 89 |
| $C_{16}H_{18}N_2O.HCl$ | 66,09 | 6,59 | 9,63 | 12,19 | 5 | 98 |
| $C_{16}H_{18}N_2O.HCl$ | 66,09 | 6,59 | 9,63 | 12,19 | 21 | 73 |

TABLE 2

9-Amino-3,3-dimethyldihydroacridine-1(2H)-ones V

| n/n 1 | R 2 | $R^1$ 3 | $R^2$ 4 | $R^3$ 5 | HX 6 | M.p., °C. 7 | IR spectrum sm$^{-1}$ 8 |
|---|---|---|---|---|---|---|---|
| 1ya | H | H | H | H | — | 223–224 | 3285, 3110, 3060, 1630, 1615, 1605, 1560, 1540 |
| 1yb | H | H | H | H | HCl | >300 | 3320, 3230, 3060, 2670, 2710, 1630, 1570, 1530 |
| 1yc | H | B | H | H | — | 247–248 | 3330, 3180, 1640, 1610, 1595, 1555, 1530 |
| 1yd | H | B | H | H | HCl | >280 | 3200, 3070, 2700, 1650, 1620, 1570, 1530 |
| 1ye | $CH_3$ | H | $CH_3$ | H | — | 142–143 | 3450, 3180, 1630, 1600, 1570, 1540 |
| 1yf | $CH_3$ | H | $CH_3$ | H | HCl | 208–209 | 3250, 3130, 1630, 1580, 1560, 1540 |
| 1yg | H | $CH_3$ | $CH_3$ | H | — | 168–170 | 3350, 3260, 3240, 3200, 3070, 1630, 1615, 1570, 1540 |
| 1yh | H | $CH_3$ | $CH_3$ | H | HCl | >270 | 3270, 3075, 2720, 1630, 1570, 1530 |
| 1yi | H | $CH_3$ | H | H | — | 244–245 | 3330, 3270, 3180, 1640, 1610, 1570, 1530 |
| 1yj | H | $CH_3$ | H | H | HCl | >280 | 3350, 3250, 3110, 2720, 1630, 1570, 1540 |
| 1yk | H | H | $CH_3$ | H | — | 174–175 | 3400, 3270, 3210, 1610, 1605, 1570, 1550 |
| 1yl | H | H | $CH_3$ | H | HCl | >280 | 3350, 3230, 1640, 1570, 1530 |
| ya | H | H | H | $C_6H_5CH_2$ | — | 169–170 | 3030, 1605, 1580, 1570, 1560, 1520 |
| yb | H | H | H | $C_6H_5CH_2$ | HCl | 231–233 | 3350, 2730, 2600, 2360, 1850, 1820, 1640, 1625, 1605, 1530 |
| yc | H | H | H | 2,4-$(CH_3)_2$ $C_6H_3CH_2$ | — | 130–132 | 3500–3100, 1620, 1580, 1560, 1520 |

| Found | | | Empirical | Calculated, % | | | Yield, |
|---|---|---|---|---|---|---|---|
| C 9 | H 10 | N 11 | Formula 12 | C 13 | H 14 | N 15 | % 16 |
| 75,35 | 7,02 | 11,66 | $C_{15}H_{16}N_2O$ | 74,97 | 6,71 | 11,66 | 96 |
| 64,96 | 6,59 | 9,71 | $C_{15}H_{16}N_2O.HCl$ | 65,10 | 6,19 | 10,12 | 90 |
| 56,38 | 4,30 | 8,47 | $C_{15}H_{15}BrN_2O$ | 56,44 | 4,74 | 8,78 | 23 |
| 50,17 | 4,64 | 7,99 | $C_{15}H_{15}BrN_2O.HCl$ | 50,66 | 4,54 | 7,88 | 96 |
| 76,11 | 7,42 | 10,35 | $C_{17}H_{20}N_2O$ | 76,09 | 7,51 | 10,44 | 85 |
| 67,43 | 7,16 | 8,70 | $C_{17}H_{20}N_2O.HCl$ | 66,99 | 6,95 | 11,63 | 97 |
| 75,71 | 7,30 | 10,21 | $C_{17}H_{20}N_2O$ | 76,09 | 7,51 | 10,44 | 99 |
| 66,61 | 6,60 | 8,70 | $C_{17}H_{20}N_2O.HCl$ | 66,99 | 6,95 | 9,19 | 94 |
| 75,09 | 6,95 | 10,84 | $C_{16}H_{18}N_2O$ | 75,56 | 7,13 | 11,02 | 98 |
| 65,88 | 6,58 | 9,61 | $C_{16}H_{18}N_2O.HCl$ | 66,09 | 6,59 | 9,63 | 92 |
| 75,67 | 7,24 | 11,06 | $C_{16}H_{18}N_2O$ | 75,56 | 7,13 | 11,02 | 97 |
| 65,77 | 6,33 | 9,30 | $C_{16}H_{18}N_2O.HCl$ | 66,09 | 6,59 | 9,63 | 94 |
| 80,21 | 6,80 | 8,23 | $C_{22}H_{22}N_2O$ | 79,95 | 6,71 | 8,48 | 88 |

TABLE 2-continued

9-Amino-3,3-dimethyldihydroacridine-1(2H)-ones V

| 71,62 | 6,52 | 10,08 | $C_{22}H_{22}N_2O \cdot HCl$ | 72,02 | 6,32 | 7,64 | 36 94 |
| 80,73 | 7,56 | 7,50 | $C_{24}H_{26}N_2O$ | 80,41 | 7,31 | 7,81 | 75 |

| 1 | 2 | 3 | 4 | 5 | 6 | 7 | 8 |
|---|---|---|---|---|---|---|---|
| yd | H | H | H | 2,4-$(CH_3)_2$–$C_6H_3CH_2$ | (Z)-$(CHCOOH)_2$ | 163–165 | 3400, 3200, 2660, 1900, 1700, 1640, 1620, 1595, 1530 |
| ye | H | H | H | 4-$ClC_6H_4CH_2$ | — | 144–145 | 3400, 3200, 1615, 1585, 1560, 1525 |
| yf | H | H | H | 4-$ClC_6H_4CH_2$ | HCl | 247 | 3360, 2600, 2450, 2350, 1850, 1650, 1630, 1610, 1590, 1580, 1530 |
| yg | H | H | H | $CH_3$ | — | 119–120 | 3200, 3120, 1615, 1580, 1570, 1530 |
| yh | H | H | H | $CH_3$ | $HCl \cdot 0,5H_2O$ | 261–262 | 3480, 3430, 3250, 3150, 2600, 1800, 1630, 1615, 1600, 1550 |
| yi | H | H | H | $C_2H_5$ | — | 145–146 | 3350, 3190, 3060, 1605, 1585, 1570, 1525 |
| yj | H | H | H | $C_2H_5$ | $HCl \cdot H_2O$ | 236–237 | 3500, 3430, 2600, 1630, 1620, 1600, 1580, 1530 |
| yk | H | H | H | $C_3H_7$ | — | 87–88 | 1615, 1595, 1570, 1530 |
| yl | H | H | H | $C_3H_7$ | $HCl \cdot 0,5H_2O$ | 205–206 | 3500, 3430, 3260, 3150, 2730, 2540, 1830, 1630, 1615, 1600, 1530 |
| ym | H | H | H | и30-$C_3H_7$ | — | 84–85 | 3350, 1615, 1600, 1570, 1530 |
| yn | H | H | H | и30-$C_3H_7$ | $HCl \cdot 0,5H_2O$ | 240–241 | 3500, 3430, 3370, 3270, 3200, 2660, 1700, 1630, 1605, 1530 |
| yo | H | H | H | $C_4H_9$ | — | 87–88 | 1625, 1610, 1600, 1570, 1530 |
| yp | H | H | H | $C_4H_9$ | $HCl \cdot H_2O$ | 220–221 | 3520, 3450, 2370, 3270, 3200, 2660, 1700, 1630, 1605, 1530 |
| yq | H | H | H | и30-$C_4H_9$ | $HCl \cdot 0,5H_2O$ | 240–241 | 3500, 3430, 3370, 3270, 3200, 2660, 1700, 1630, 1605, 1530 |
| yr | H | H | H | $(C_2H_5)_2N$–$CH_2CH_2$ | 2HCl | 264–265 | 3250, 3150, 2600, 2430, 1830, 1690, 1640, 1620, 1590, 1540 |

| 9 | 10 | 11 | 12 | 13 | 14 | 15 | 16 |
|---|---|---|---|---|---|---|---|
| 70,71 | 6,50 | | $C_{24}H_{26}N_2O \cdot C_4H_4O_4$ | 70,87 | 6,37 | | 78 |
| 72,48 | 5,97 | 7,99 | $C_{22}H_{21}ClN_2O$ | 72,42 | 5,80 | 7,68 | 96 |
| 66,32 | 5,96 | 6,98 | $C_{22}H_{21}ClN_2O \cdot HCl$ | 65,84 | 5,53 | 6,98 | |
| 75,68 | 7,47 | 10,66 | $C_{16}H_{18}N_2O$ | 75,56 | 7,13 | 11,01 | 76 |
| 64,20 | 6,81 | 9,20 | $C_{16}H_{18}N_2O \cdot HCl \cdot 0,5H_2O$ | 64,10 | 6,72 | 9,34 | 88 |
| 75,82 | 7,38 | 10,79 | $C_{17}H_{20}N_2O$ | 76,09 | 7,51 | 10,44 | 91 |
| 63,56 | 7,26 | 8,43 | $C_{17}H_{20}N_2O \cdot HCl \cdot H_2O$ | 63,25 | 7,18 | 8,68 | 90 |
| 76,12 | 8,25 | 9,69 | $C_{18}H_{22}N_2O$ | 76,56 | 7,85 | 9,92 | 45 |
| 66,27 | 7,60 | 8,61 | $C_{18}H_{22}N_2O \cdot HCl \cdot 0,5H_2O$ | 65,94 | 7,38 | 8,54 | 92 |
| 76,75 | 7,67 | 9,59 | $C_{18}H_{22}N_2O$ | 76,56 | 7,85 | 9,92 | 62 |
| 66,29 | 7,64 | 8,25 | $C_{18}H_{22}N_2O \cdot HCl \cdot 0,5H_2O$ | 65,94 | 7,38 | 8,54 | 89 |
| 77,45 | 8,37 | 9,79 | $C_{19}H_{24}N_2O$ | 76,99 | 8,16 | 9,45 | 74 35 |
| 65,37 | 8,15 | 8,15 | $C_{19}H_{24}N_2O \cdot HCl \cdot H_2O$ | 65,04 | 7,36 | 7,98 | 83 |
| 66,29 | 7,64 | 8,25 | $C_{19}H_{24}N_2O \cdot HCl \cdot 0,5H_2O$ | 65,94 | 7,38 | 8,54 | 88 |
| 61,49 | 7,80 | 9,71 | $C_{21}H_{29}N_3O \cdot 2HCl$ | 61,16 | 7,58 | 10,19 | 28 |

TABLE 2-continued

9-Amino-3,3-dimethyldihydroacridine-1(2H)-ones V

| 1 | 2 | 3 | 4 | 5 | 6 | 7 | 8 |
|---|---|---|---|---|---|---|---|
| ys | H | H | H | $C_4H_9$ | (Z)-CHCOOH)$_2$ | 156–157 | 3400, 2650, 1850, 1640, 1620, 1600, 1540 |
| yt | H | H | H | $C_4H_9$ | HOOCCH$_2$CH$_2$COOH | 111–113 | 2700–2400, 1920, 1700, 1650, 1620, 1600, 1540 |
| yu | H | H | H | $C_4H_9$ | 2-HOC$_6$H$_4$COOH | 129–130 | 2550, 1930, 1660, 1640, 1620, 1600, 1570, 1540 |
| yv | H | H | H | $C_4H_9$ | (COOH-CH=CH-C(=O)-N(H)-C(=O)-NH) | 224–225 | 3170, 3040, 2650, 1930, 1720, 1670, 1610, 1530 |
| yw | H | H | H | $C_4H_9$ | HO-C(CH$_2$COOH)$_2$-COOH | 151(pa3π) | 3470, 2600, 1960, 1720, 1650, 1620, 1600, 1570, 1540 |
| yx | H | H | H | $C_4H_9$ | HOOCCOOH | 149–151 | 2650, 1900, 1720, 1640, 1620, 1600, 1540 |
| yy | H | H | H | $C_4H_9$ | H$_3$PO$_4$.3H$_2$O | 225–226 | 2650, 2400, 1930, 1640, 1620, 1605, 1535 |
| yz | H | H | H | $C_4H_9$ | H$_2$SO$_4$.H$_2$O | 178–179 | 3370, 3070, 1640, 1620, 1605, 1540 |
| yaa | H | H | H | $C_4H_9$ | 5-NO$_2$-2-Cl—C$_6$H$_3$COOH | 146–147 | 2350, 1950, 1660, 1630, 1610, 1540, 1520 |
| ybb | H | H | H | $C_5H_{11}$ | — | 72–73 | 1620, 1590, 1570, 1520 |
| ycc | H | H | H | $C_5H_{11}$ | HCl | 206–208 | 2520, 1870, 1630, 1615, 1520 |

| 9 | 10 | 11 | 12 | 13 | 14 | 15 | 16 |
|---|---|---|---|---|---|---|---|
| 66,57 | 6,84 |  | $C_{19}H_{24}N_2O.C_4H_4O_4$ | 66,97 | 6,84 |  | 89 |
| 66,28 | 7,04 |  | $C_{19}H_{24}N_2O.C_4H_6O_4$ | 66,65 | 7,30 |  | 92 |
| 71,39 | 6,87 |  | $C_{19}H_{24}N_2O.C_7H_6O_3$ | 71,87 | 6,96 |  | 85 |
| 63,60 | 6,44 |  | $C_{19}H_{24}N_2O.C_5H_4N_2O_4$ | 63,70 | 6,24 |  | 88 |
| 61,89 | 6,90 |  | $C_{19}H_{24}N_2O.C_6H_8O_7$ | 61,46 | 6,60 |  | 93 |
| 65,75 | 6,93 |  | $C_{19}H_{24}N_2O.C_2H_2O_4$ | 65,27 | 6,78 |  | 91 |
| 50,52 | 7,13 |  | $C_{19}H_{24}N_2O.H_3PO_4.3H_2O$ | 50,88 | 7,42 |  | 76 |
| 54,93 | 6,90 |  | $C_{19}H_{24}N_2O.H_2SO_4.H_2O$ | 55,32 | 6,84 |  | 95 |
| 62,65 | 5,87 |  | $C_{19}H_{24}N_2O.C_7H_4ClNO_4$ | 62,71 | 5,67 |  | 87 |
| 77,79 | 8,70 | 8,76 | $C_{20}H_{26}N_2O$ | 77,38 | 8,44 | 9,02 | 42 |
| 69,62 | 7,70 | 7,60 | $C_{20}H_{26}N_2O.HCl$ | 69,25 | 7,85 | 8,08 | 91 |

TABLE 3

9-Amino-3,3-dimethyl-1,2,3,4-tetrahydroacridine-1ols YI[a)]

| YI n/n 1 | R$^3$ 2 | HX 3 | M.p., °C. 4 | IR spectrum ν, sm$^{-1}$ 5 |
|---|---|---|---|---|
| YIa | H | — | 200–202 | 3370,3195,3040, 1645,1585,1575 |
| YIB | H | (Z)-HOOCCH=CHCOOH | 150–152 | 3480,3320,3100, 1615,1560,1495 |
| YIc | $C_4H_9$ | — | 142–143 | 3300,3200–2500 1610,1570,1555 |
| YId | $C_4H_9$ | (Z)-HOOCCH=CHCOOH | 133–134 | 3240,3150,3100, 3050,2740,2640, 1640,1585,1525 |

TABLE 3-continued

9-Amino-3,3-dimethyl-1,2,3,4-tetrahydroacridine-1ols YI[*]

| | | | | |
|---|---|---|---|---|
| YIe | $C_6H_5CH_2$ | — | 175–176 | 3380,3220,3060, 3040,1610,1580, 1550,1520 |
| YIf | $C_6H_5CH_2$ | (Z)-HOOCCH=CHCOOH | 170–171 | 3310,2700,1640, 1610,1590,1560, 1530 |
| YIg | $4\text{-}ClC_6H_4CH_2$ | — | 179–180 | 3380,3160,1615, 1580,1560 |
| YIh | $4\text{-}ClC_6H_4CH_2$ | (Z)-HOOCCH=CHCOOH | 171–172 | 3260,3090,3040, 2700,1640,1610, 1570,1520 |
| YIi | $2,4\text{-}(CH_3)_2C_6H_4CH_2$ | — | 89–90 | 3300,3230,3060, 1620,1580,1560, 1510,1495 |
| YIj | $2,4\text{-}(CH_3)_2C_6H_4CH_2$ | (Z)-HOOCCH=CHCOOH | 155 (разл.) | 3260,3230,3150, 3090,3040,1680 1630,1610,1580, 1530 |

| Found, % | | | | Calculated, % | | | Yield, |
|---|---|---|---|---|---|---|---|
| C | H | N | Empirical Formula | C | H | N | % |
| 6 | 7 | 8 | 9 | 10 | 11 | 12 | 13 |
| 74.37 | 7,89 | 11,45 | $C_{15}H_{18}N_2O$ | 74,35 | 7,49 | 11,56 | 87 |
| 64.15 | 6,63 | 7,78 | $C_{15}H_{18}N_2O \cdot C_4H_4O_4$ | 63,67 | 6,19 | 7,82 | 93 |
| 76.57 | 9,08 | 9,40 | $C_{19}H_{26}N_2O$ | 76,47 | 8,78 | 9,39 | 96 |
| 66.65 | 7,65 | 6,53 | $C_{19}H_{26}N_2O \cdot C_4H_4O_4$ | 66,65 | 7,30 | 6,76 | 89 |
| 79.54 | 7,41 | 8,02 | $C_{22}H_{24}N_2O$ | 79,48 | 7,28 | 8,43 | 96 |
| 69,54 | 6,48 | 6,34 | $C_{22}H_{24}N_2O \cdot C_4H_4O_4$ | 69,63 | 6,29 | 6,25 | 82 |
| 71,78 | 6,48 | 7,69 | $C_{22}H_{23}ClN_2O$ | 72,02 | 6,32 | 7,64 | 95 |
| 64,88 | 5,80 | 5,71 | $C_{22}H_{23}ClN_2O \cdot C_4H_4O_4$ | 64,66 | 5,64 | 5,80 | 87 |
| 79,61 | 8,28 | 7,30 | $C_{24}H_{28}N_2O$ | 79,96 | 7,83 | 7,77 | 93 |
| 70,66 | 7,12 | 5,64 | $C_{24}H_{28}N_2O \cdot C_4H_4O_4$ | 70,57 | 6,77 | 5,88 | 86 |

[*] $R=R^1=R^2=H$

TABLE 4

9-Amino-3,3-dimethyl-3,4-dihydroacridines[y11*]

| n/n | $R^3$ | HX | M.p. °C. | IR spectrum v, sm$^{-1}$ |
|---|---|---|---|---|
| 1 | 2 | 3 | 4 | 5 |
| y11a | H | — | 154–155 | 3320, 3140, 1645, 1570 |
| y11b | H | HCl | 300 | 3330, 3170, 2760, 1650, 1630, 1590, 1560, 1540 |
| y11c | $C_4H_9$ | HCl | 192–193 | 3240, 2710, 2650, 1630, 1620, 1610, 1560, 1530 |
| y11d | $4\text{-}ClC_6H_4CH_2$ | HCl | 222–223 | 3230, 3100, 2730, 1630, 1620, 1600, 1545, 1525 |
| y11e | $C_6H_5CH_2$ | HCl | 236–237 | 3190, 3100, 3060, 3030, 2720, 1625, 1600, 1550 |
| y11f | $C_6H_5CH_2$ | $HOOCCH_2CH_2COOH$ | 93–94 | 3340, 2600, 1920, 1720, 1710, 1650, 1620, 1570, 1660, 1540 |
| y11g | $C_6H_5CH_2$ | pyridine-COOH | 137–138 | 3250, 2550 |

TABLE 4-continued

9-Amino-3,3-dimethyl-3,4-dihydroacridines[y11*]

| | | | | |
|---|---|---|---|---|
| y11h | $C_6H_5CH_2$ | 4-pyridyl-COOH | 151–152 | 3220, 2550, 1940, 1650, 1620, 1570, 1550, 1530 |
| y11i | $C_6H_5CH_2$ | 2-$HOC_6H_4COOH$ | 134–135 | 3250, 3060, 2650, 1940, 1620, 1605, 1580, 1550 |
| y11j | $C_6H_5CH_2$ | (maleimide-COOH) | 220–221 | 3280, 3130, 2600, 1940, 1705, 1670, 1650, 1630, 1610, 1570, 1530 |
| y11k | $C_6H_5CH_2$ | citric acid (HO-C(CH$_2$COOH)$_2$-COOH) | 104–105 | 3430, 3375, 2620, 2040, 1950, 1670, 1650, 1630, 1570, 1560, 1525 |

| Found, % | | | Empirical | Calculated, % | | | Yield, |
|---|---|---|---|---|---|---|---|
| C | H | N | Formula | C | H | N | % |
| 6 | 7 | 8 | 9 | 10 | 11 | 12 | 13 |
| 80,15 | 7,05 | 12,31 | $C_{15}H_{16}N_2$ | 80,32 | 7,19 | 12,49 | 98 |
| 68,71 | 6,58 | 10,51 | $C_{15}H_{16}N_2 \cdot HCl$ | 69,09 | 6,57 | 10,74 | 96 |
| 71,96 | 7,95 | 8,53 | $C_{19}H_{24}N_2 \cdot HCl$ | 72,02 | 7,95 | 8,84 | 95 |
| 68,74 | 5,44 | 7,45 | $C_{22}H_{21}ClN_2 \cdot HCl$ | 68,57 | 5,76 | 7,27 | 96 |
| 75,06 | 6,64 | 7,62 | $C_{22}H_{22}N_2 \cdot HCl$ | 75,31 | 6,61 | 7,98 | 96 |
| 72,03 | 6,88 | | $C_{22}H_{22}N_2 \cdot C_4H_6O_4$ | 72,20 | 6,52 | | 99 |
| 76,87 | 6,10 | | $C_{22}H_{22}N_2 \cdot C_6H_5NO_2$ | 76,86 | 6,22 | | 90 |
| 76,42 | 6,60 | | $C_{22}H_{22}N_2 \cdot C_6H_5NO_2$ | 76,86 | 6,22 | | 82 |
| 76,58 | 6,12 | | $C_{22}H_{22}N_2 \cdot C_7H_6O_3$ | 76,97 | 6,24 | | 83 |
| 69,02 | 5,91 | | $C_{22}H_{22}N_2 \cdot C_5H_4N_2O_4$ | 68,92 | 5,57 | | 98 |
| 65,98 | 6,32 | | $C_{22}H_{22}N_2 \cdot C_6H_8O_7$ | 66,39 | 5,97 | | 99 |

| 1 | 2 | 3 | 4 | 5 |
|---|---|---|---|---|
| y11l | $C_6H_5CH_2$ | $C_6H_5COOH$ | 128–129 | 3220, 2400, 1950, 1650, 1620, 1570, 1530 |
| y11m | $C_6H_5CH_2$ | $C_6H_5CH_2COOH$ | 103–104 | 3230, 2500, 1920, 1650, 1620, 1570, 1550, 1525 |
| y11n | $C_6H_5CH_2$ | 4-$HOC_6H_4CH_2CH_2COOH \cdot H_2O$ | 122–123 | 3550, 3230, 2660, 2600, 1940, 1650, 1610, 1570, 1540 |
| y11o | $C_6H_5CH_2$ | HOOCCOOH; 0,5$H_2O$ | 191–192 | 3320, 3100–2500, 1920, 1720, 1690, 1630, 1620, 1590, 1580, 1550, 1520 |
| y11p | $C_6H_5CH_2$ | $HOOCCH_2COOH$ | 130–131 (разл.) | 3280, 2600, 1950, 1620, 1560, 1530 |
| y11q | $C_6H_5CH_2$ | $H_3PO_4 \cdot 3H_2O$ | 234–235 | 3280, 3100–2600, 2400, 1630, 1620, 1600, 1570, 1525 |
| y11r | $C_6H_5CH_2$ | $H_2SO_4 \cdot 1,5H_2O$ | 161–162 | 3280–3000, 2700–2400, 1630, 1620, 1600, 1570, 1530 |
| y11s | $C_6H_5CH_2$ | 5-$NO_2$-2-$ClC_6H_3COOH$ | 200–21 | 3250, 2700–2400, 1950, 1660, 1620, 1610, 1570, 1515 |
| y11t | $C_6H_5CH_2$ | $CH_3C(O)NHCH_2COOH$ | 137–138 | 3340, 3260, 2700–2400; 1980, 1660, 1630, 1590, 1560 |

TABLE 4-continued

| \multicolumn{8}{c}{9-Amino-3,3-dimethyl-3,4-dihydroacridines[y11*]} |
| --- | --- | --- | --- | --- | --- | --- | --- |
| y11u | $C_6H_5CH_2$ | (Z)-HOOCCH=CHCOOH | 146–147 | \multicolumn{4}{l}{3270, 2650, 1900, 1680, 1640, 1610, 1570, 1530} |
| 6 | 7 | 8 | 9 | 10 | 11 | 12 | 13 |
| 79,80 | 6,43 | | $C_{22}H_{22}N_2 \cdot C_7H_6O_2$ | 79,79 | 6,46 | | 92 |
| 79,52 | 6,78 | | $C_{22}H_{22}N_2 \cdot C_8H_8O_2$ | 79,97 | 6,71 | | 85 |
| 74,76 | 7,11 | | $C_{22}H_{22}N_2 \cdot C_9H_{10}O_3 \cdot H_2O$ | 74,67 | 6,87 | | 86 |
| 69,60 | 6,21 | | $C_{22}H_{22}N_2 \cdot C_2H_2O_4 \cdot 0,5H_2O$ | 69,72 | 6,09 | | 81 |
| 72,08 | 6,60 | | $C_{22}H_{22}N_2 \cdot C_3H_4O_4$ | 71,75 | 6,26 | | 68 |
| 56,48 | 6,45 | | $C_{22}H_{22}N_2 \cdot H_3PO_4 \cdot 3H_2O$ | 56,55 | 6,70 | | 95 |
| 60,07 | 6,36 | | $C_{22}H_{22}N_2 \cdot H_2SO_4 \cdot 1,5H_2O$ | 60,11 | 6,19 | | 86 |
| 67,25 | 5,19 | | $C_{22}H_{22}N_2 \cdot C_7H_4ClNO_4$ | 67,50 | 5,08 | | 92 |
| 72,04 | 6,48 | | $C_{22}H_{22}N_2 \cdot C_4H_7NO_3$ | 72,37 | 6,77 | | 96 |
| 72,15 | 6,22 | | $C_{22}H_{22}N_2 \cdot C_4H_4O_4$ | 72,54 | 6,09 | | 98 |

*) $R = R^1 = R^2 = H$

The influence of drugs on reflex conditioning in rats was studied by the passive avoidance test in conditions of 50% acquisition. The effect of the compound was estimated by the increase of the relative number of learned animals with respect to that of control group. The test substances were injected intraperitoneally 20 min before training in the dose of 0.1 mg/kg, at dose the reference drug amiridine was effective in the passive avoidance test. The other reference drug—noothropic agent piracetam—was given in the dose 250 mg/kg 60 min before training. Amnestic syndrome was stimulated by 20 days application of Sc at the daily dose of 1 mg/kg intraperitoneally. To assess the autiamnestic effects of the claimed compounds, the compounds and the reference drugs they were applied in the course of 10 days immediately following cancellation of scopolamine injection. The passive avoidance test was performed within 24 hours after the last application of test preparations.

Contractile activity of isolated smooth muscle organs (guinea-pig ilium, rat testicles) under the action of test substances was studied by the method of Blattner with the use of ACh and adrenaline.

Acetylcholinesterase inhibition under the action of preparations was assessed by the spectrophotometric technique of Ellman on the enzyme from human erythrocytes.

Ionic permeabilities of excitable membranes under the action of drugs were studied by the voltage clamp technique in the Ranvier node of the frog.

Microviscosity of membranes of brain synaptosomes was studied with the use of molecular probe pirren. Brain tissue homogenization and preparation of synaptosomes were performed by the method of De Robertis.

Since the substances in question are the derivatives of aminoacridine, tacrine has been also used as a reference drug along with amiridine and piracetam.

The results of the study of pharmacological activity of substances in question are summarized in Table 5. All the substances can be attributed to the class of moderately and low toxic ones since LD varied in the limits of 40–1000 mg/kg being greater than 100 mg/kg in the main group of substances which is a substantial advantage with respect to reference drugs amiridine and tactine having LD 35 and 52 mg/kg, respectively.

The main group of substances increased moter activity by 40–90. Test substances magnified the effect of arecoline by 30–66% indicating to the involvement of cholinergic mechanisms in their pharmacological activity, through their ability to inhibit acetylcholinesterase was less pronounced than that of the reference drugs. They did not effect the contractile activity of smooth muscles in contrast to amiridine. Therefore their side effects of cholinergic origin (tremor, salivation, diarrea) are less expressed in comparison with reference drug and were observed only at toxic doses. There was no substautial influence of test preparations on the effects of hexenal and apomorphine.

As revealed by passive avoidance test most of the substances (IVf, Vd, Vu, VIk, VIIb, VIId, VIIe, VIIi, VIII, VIIo, VIIp, VIIq, and VIIr) statistically significantly improved performance of normal rats, the substances Vd, VIId, VIIe being as effective in improving learning and memory as amiridine and piracetam. However they have an advantage over amiridine as being of low toxicity.

The results of the Step-down test with scopolamine induced amnesia in mice are presented in Table 6. The substances VIIe, Vp, VIIb, VIIi, and Vaa showed pronounced antiatonestic activity, comparable with that of amiridine and tacrine.

The therapeutic effects of amiridine and tactine are commonly attributed to their ability to block potassium permeability and to inhibit acetylcholinesterase. However the data of Table 6 suggest that the drugs antiamnestic activity is most closely related to their ability to induce the shift of potassium permeability activation region to the hyperpolarizing values of membrane potential. In vivo conditions this effect may be tantamount to the increase of resting membrane potential of nerve cells thus providing more safe generation of action potential especially in nerve cells with decreased excitability. The effect may provide a new approach in the search for drugs with antiamnestic activity.

TABLE 5

Pharmacological effects of aminoacridine derivatives

| No. 1 | Substance designation 2 | $LD_{50}$ (mg/kg) by Kerber 3 | Acetylcholinesterase inhibition $IC_{50}(M)$ 4 | Motor activity increment (% to control) 5 | Increase of duration of arecoline induced hyperkynesis (% to control) 6 | Increase of the number of correct trails (% to control). Passive avoidance test (rats) 7 |
|---|---|---|---|---|---|---|
| 1. | IVb | 70.0 ± 4.3 | $3.5 \cdot 10^{-6}$ | 0 | 33* | 30 |
| 2. | IVd | >500 | $5.0 \cdot 10^{-5}$ | 15 | 20 | 0 |
| 3. | IVf | 40.0 ± 1.2 | $1.3 \cdot 10^{-5}$ | 0 | 0 | 0 |
| 4. | IVh | >500 | $3.0 \cdot 10^{-5}$ | 0 | 20 | 0 |
| 5. | IVl | 616.7 ± 23.7 | $6.3 \cdot 10^{-7}$ | 57* | 0 | 0 |
| 6. | IVj | 63.6 ± 8.7 | $3.0 \cdot 10^{-5}$ | 0 | 30* | 0 |
| 7. | Vb | 735.0 ± 21.8 | no effect | 80* | 15 | 25 |
| 8. | Vd | >1000 | $1.0 \cdot 10^{-5}$ | 90* | 0 | 50* |
| 9. | Vf | >1000 | $8.0 \cdot 10^{-5}$ | 13 | 0 | 0 |
| 10. | Vh | 65.8 ± 4.8 | $4.0 \cdot 10^{-7}$ | 40* | 20 | 0 |
| 11. | Vj | 73.3 ± 8.6 | $1.7 \cdot 10^{-6}$ | 59* | 20 | 0 |
| 12. | Vl | 283.3 ± 35.7 | $3.0 \cdot 10^{-6}$ | 74* | 30* | 0 |
| 13. | Vn | 70.2 ± 7.3 | $6.0 \cdot 10^{-6}$ | 76* | 0 | 0 |
| 14. | Vp | 200.0 ± 21.9 | $2.5 \cdot 10^{-5}$ | 69* | 0 | 25 |
| 15. | Vq | 158.3 ± 21.9 | $2.0 \cdot 10^{-6}$ | 75* | 0 | 0 |
| 16. | Vr | 135.0 ± 8.2 | $5.0 \cdot 10^{-5}$ | 0 | 26 | 0 |
| 17. | Vs | 165.8 ± 14.8 | $7.0 \cdot 10^{-6}$ | 0 | 0 | 15 |
| 18. | Vt | 210.0 ± 9.8 | $7.0 \cdot 10^{-6}$ | 0 | 0 | 0 |
| 19. | Vu | 210.0 ± 5.8 | $6.0 \cdot 10^{-6}$ | 20 | 0 | 30* |
| 20. | Vv | 433.3 ± 7.8 | $7.0 \cdot 10^{-6}$ | 26 | 15 | 25 |
| 21. | Vw | 125.0 ± 11.8 | $7.0 \cdot 10^{-6}$ | 10 | 10 | 10 |
| 22. | Vx | 121.7 ± 15.5 | $1.0 \cdot 10^{-5}$ | 0 | 0 | 25 |
| 23. | Vy | 210.0 ± 14.8 | $7.0 \cdot 10^{-6}$ | 0 | 0 | 0 |
| 24. | Vz | 200.0 ± 21.9 | $7.0 \cdot 10^{-6}$ | 0 | 0 | 20 |
| 25. | Vaa | 650.0 ± 11.3 | $7.0 \cdot 10^{-6}$ | 26 | 25 | 15 |
| 26. | VIb | 63.3 ± 8.8 | $1.2 \cdot 10^{-6}$ | 40* | 66* | 20 |
| 27. | VIg | 80.0 ± 2.7 | $0.3 \cdot 10^{-5}$ | 40* | 36* | 0 |
| 28. | VIi | 75.0 ± 1.2 | $1.0 \cdot 10^{-6}$ | 13 | 46* | 15 |
| 29. | VIj | 33.4 ± 3.2 | $2.5 \cdot 10^{-6}$ | 55* | 13 | 40* |
| 30. | VIe | 50.0 ± 8.6 | $1.3 \cdot 10^{-6}$ | 64* | 15 | 0 |
| 31. | VIIb | 37.5 ± 0.9 | $7.5 \cdot 10^{-8}$ | 41* | 25 | 40* |
| 32. | VIIc | 33.3 ± 4.4 | $0.6 \cdot 10^{-6}$ | 20 | 15 | 25 |
| 33. | VIId | 125.8 ± 8.9 | $0.6 \cdot 10^{-8}$ | 28 | 15 | 60* |
| 34. | VIIe | 158.3 ± 21.9 | $1.2 \cdot 10^{-6}$ | 32 | 12 | 50* |
| 35. | VIIu | 83.8 ± 5.6 | $2.3 \cdot 10^{-6}$ | 15 | 12 | 0 |
| 36. | VIIf | 125.0 ± 15.5 | $6.1 \cdot 10^{-6}$ | 0 | 0 | 0 |
| 37. | VIIg | 200.0 ± 21.9 | $5.0 \cdot 10^{-7}$ | 23 | 0 | 0 |
| 38. | VIIh | 116.7 ± 10.9 | $5.0 \cdot 10^{-7}$ | 13 | 28 | 20 |
| 39. | VIIi | 500 | $1.0 \cdot 10^{-6}$ | 20 | 15 | 35* |
| 40. | VIIk | 90.5 ± 8. | $2.0 \cdot 10^{-6}$ | 20 | 20 | 25 |
| 41. | VIII | 116.7 ± 10.9 | $8.0 \cdot 10^{-7}$ | 10 | 15 | 40* |
| 42. | VIIm | 112.5 ± 10.9 | $2.7 \cdot 10^{-6}$ | 15 | 15 | 25 |
| 43. | VIIn | 125.0 ± 10.9 | $6.3 \cdot 10^{-7}$ | 11 | 46* | 40 |
| 44. | VIIo | 62.5 ± 7.7 | $2.5 \cdot 10^{-6}$ | 16 | 0 | 40* |
| 45. | VIIp | 75.0 ± 3.8 | $8.5 \cdot 10^{-7}$ | 33 | 21 | 45* |
| 46. | VIIq | 73.3 ± 4.4 | $6.3 \cdot 10^{-7}$ | 20 | 30* | 45* |
| 47. | VIIr | 69.5 ± 5.6 | $8.5 \cdot 10^{-7}$ | 0 | 0 | 45* |
| 48. | Amiridine | 52.0 ± 3.4 | $1.5 \cdot 10^{-7}$ | 45* | 100* | 70* |
| 49. | Tacrine | 35.5 ± 1.8 | $3.8 \cdot 10^{-7}$ | 0 | 88* | 25 |
| 50. | Piracetam | 1000 | no effect | 0 | 0 | 63* |

\* - statistically significant, $p < 0.05$

TABLE 6

Antiamnestic activity and some physiological effect of new aminoacridine derivatives

| Substance | Antiamnestic activity in Step-down test (% of mice with latency > cut off) | Block of K-channels IC (M) | AChE inhibition IC (M) | The shift of activation region of K channels Substance lowest concentrations in M. producing measureable shift of 1–2 mV |
|---|---|---|---|---|
| VIIe | 25 | 1 10 | 1.2 10 | <10 |
| VIb | 0 | 1 10 | 1.2 10 | <10 |
| Vf | 0 | 5 10 | 8.0 10 | no effect |
| Vp | 25 | 1 10 | 2.5 10 | <10 |
| IVb | 0 | no effect | 3.5 10 | no effect |
| VIId | 20 | 1 10 | 6.0 10 | <10 |
| Vd | 20 | 1 10 | 1.0 10 | <10 |
| VIIb | 25 | no effect | 7.5 10 | <10 |
| VIj | 0 | 1 10 | 3.0 10 | no effect |
| VIi | 0 | 1 10 | 1.0 10 | no effect |
| Vb | 0 | 1 10 | no effect | no effect |
| VIIi | 25 | 3 10 | 1.0 10 | <10 |
| Vaa | 25 | 5 10 | 7.0 10 | <10 |
| Tacrine | 33 | 5 10 | 3.5 10 | <10 |
| Amiridine | 33 | 5 10 | 1.5 10 | <10 |

TABLE 7

Antiamnestic activity of substance Vp in rats on the model of amnestic syndrome

| Drug, duration of application (in days) | Dose (mg/kg) | Passive avoidance latency (sec) | Microviscosity changes in % to control |
|---|---|---|---|
| Control | — | 160.0 + 12.4 | 100 |
| Scopolamine (Sc) 20 + 10 (saline) | 1 | 70.4 + 10.5* | 131.2* |
| Sc + Vp 20 + 10 | 1 + 1 | 170.3 + 14.9ˣ | 93.8 |
| Sc + amiridine 20 + 10 | 1 + 1 | 149.0 + 11.7ˣ | 105.0ˣ |
| Sc + tacrine 20 + 10 | 1 + 1 | 169.0 + 14.8 | 97.2ˣ |
| Sc + piracetam 20 + 10 | 1 + 250 | 162.3 + 13.3ˣ | 102.6ˣ |

*$p < 0.05$ with respect to control group
ˣ$p < 0.05$ with respect to scopolamine group

TABLE 8

Antiamnestic activity of Vp substance in old rats

| Drug, duration of application (in days) | Dose (mg/kg) | Passive avoidance latency in 7 days after training (sec) | Microviscosity changes (% to control) | Cholesterol content in synaptosomes (% from total lipid content) |
|---|---|---|---|---|
| Control I (3 month) | — | 109.6 + 24.7 | 100 | 28.2 + 2.2 |
| Control II (18 month) | — | 47.5 + 13.3* | 132* | 39.6 + 0.7* |
| Vp (20) | 1 | 169.4 + 10.5ˣ | 97.9ˣ | 30.1 + 2.4ˣ |
| Amiridine (20) | 1 | 116.1 + 16.9ˣ⁺ | 101.7ˣ | 33.2 + 0.8ˣ |
| Tacrine (20) | 1 | 163.4 + 16.5ˣ | 101.4ˣ | 39.7 + 1.4* |
| Piracetam (20) | 250 | 120.0 + 24.3*⁺ | 101.8ˣ | 35.1 + 1.0* |

\* - $p < 0.05$ with respect to control I
ˣ - $p < 0.05$ with respect to control II
⁺ - $p < 0.05$ with respect to Vp group For more detailed study the substance Vp was chosen because of its most pronounced capability to induce the shift of potassium permeability voltage dependency and substautial amnestic activity with lower toxicity (LD=200–22 mg/kg) than that of amiridine and tactine. On the model of atonestic syndrome induced by multiple scopolamine injection substance Vo improved performance in passive avoidance test in the 10 days application course to the level achieved under the treatment with reference drugs (Table 7). The improvement of reflex conditioning was accompanied by the normalizing of microviscosity of brain synaptosomes increased in the animals with amnestic syndrome.

Table 8 illustrates the data obtained with the use of old rats. 20 days course of treatment with substance Vp improved performance of old rats (age 18 months) in passive avoidance test more significantly than in 6 month old adult rats, while the reference drugs improved the learning and memory only to the level achieved in 6 month old rats. Improvement of animal performance was accompanied by the normalizing of brain synaptosomes microviscosity under the action of all the substances tested. In addition to that amiridine and substance Vp normalized the cholesterol content of brain synaptosomes. The latter observation indicates to the possible interference of amiridine and substance Vo into the processes of atherogenesis in old animals.

Lipid regulative activity of the declared compounds—derivatives of 9-amino acridine—were evaluated in vitro—were evaluated in vitro using rat adipocytes. Adipocytes were separated from adipose tissue of testis appendages of adult male rats. Lipid composition analysis was performed by the method of thin-layer chromatography.

Quantitative analysis of phospholipids (PL), mono- and diacylglycerides (MDG), triacylglycerides (TG), free fatty acids (FFA), free cholesterol (FCL), and methyl esters of fatty acids (MEFA) was performed by the method of spectrophotometry.

The results Of studies of lipid-regulative activity of the declared compounds and probucol—the drug widely used to treat atherosclerosis (Duckley M. M. - T., Goa K. L., Price A. H., Bfogden R. N. Drugs, 1989, 37, 761–800) are presented in Tables 9–13.

Compounds VIIe, Vo and VIId possess the most potent effect on lipid composition of adipocytes (in absolute parameters and in relations of separate fractions).

Compound VIIe. Under the effect of this compound in adipocytes phospholipids content increase and simultaneous decrease of triglycerides content takes place (Table 9). The content of methyl esters of fatty acids is decreased. Increase of PL/TG ratio (Table 11) probably takes place not only at the expense of lipid synthesis in cells (Tables 10, 12) but also due to ejection of triacylglycerides into the external medium with simultaneous retention of phospholipids in a cell (Tables 10, 12, 13). A tendency towards increase of relative cholesterol ejection from a cell is observed (Table 10, 12).

TABLE 9

Lipid composition of adiposytes (%) after incubation in the presence of the compounds of the aminoacridine series.
PL - phospholipids, CL - cholesterol, FFA - free fatty acids, TG - triglycerides, MEFA - methyl esher of fatty acids.

| Compounds | PL | CL | FFA | TG | MEFA |
|---|---|---|---|---|---|
| control | 15,5–0,5 | 21,3–0,6 | 22,2–0,3 | 23,5–0,4 | 18,9–0,6 |
| ethanol | 14,8–0,6 | 21,0–0,5 | 21,1–0,5 | 24,1–0,5 | 18,7–0,7 |
| VIIe | 21,5–2,3 | 22,6–1,7 | 20,3–0,6 | 20,3–1,9 | 15,3–1,6 |
| VIj | 18,1–1,7 | 22,5–1,0 | 23,0–0,8 | 21,2–1,3 | 15,2–0,6 |
| Vp | 19,1–1,0 | 22,9–1,9 | 22,1–0,9 | 21,5–1,9 | 14,2–0,9 |
| VIId | 15,5–2,6 | 22,4–1,0 | 24,5–0,7 | 21,2–1,3 | 15,7–0,8 |
| Vaa | 14,1–0,5 | 22,3–1,3 | 22,8–0,6 | 24,2–0,7 | 16,6–0,8 |
| VIIi | 18,5–1,2 | 22,2–0,4 | 21,4–0,5 | 21,4–0,2 | 16,4–0,7 |
| VIIj | 13,9–1,7 | 22,8–0,9 | 22,4–2,4 | 24,1–0,6 | 16,8–0,6 |
| VIIk | 17,0–1,8 | 22,8–2,2 | 21,8–1,8 | 21,8–1,4 | 16,7–2,8 |
| probucol | 15,5–0,6 | 18,3–1,3 | 24,3–0,6 | 22,6–1,1 | 19,1–1,3 | n = 19 for control and ethanol. In all the rest cases n = 3.
*statistically reliable differences (in comparison with ethanol), p < 0,05.

TABLE 10

Lipid content (%) in incubation medium after incubation of adipocytes in the presence of the compounds of aminoacridine series.
PL - phospholipids, MDG - mono- and diglycerides, CL - cholesterol, FFA - free fatty acids, TG - triglycerides.

| Compounds | PL | MDG | CL | FFA | TG |
|---|---|---|---|---|---|
| control | 15,3–0,5 | 18,5–0,5 | 19,0–0,3 | 23,1–0,5 | 23,9–0,5 |
| ethanol | 15,9–0,5 | 17,8–0,6 | 19,7–0,5 | 23,0–0,7 | 23,2–0,5 |
| VIIe | 14,9–1,5 | 15,3–2,3 | 20,3–1,5 | 24,1–1,5 | 25,3–1,1 |
| VIj | 14,6–2,1 | 15,3–0,9 | 22,3–1,1* | 24,2–1,4 | 23,4–1,4 |
| Vp | 13,5–0,9 | 16,0–0,7 | 20,9–1,2 | 23,7–1,1 | 25,8–1,5 |
| VIId | 16,0–0,6 | 16,1–0,7 | 21,2–0,7 | 22,8–0,8 | 23,7–0,3 |
| Vaa | 13,5–0,4 | 20,4–2,8 | 18,8–0,6 | 22,6–1,5 | 24,6–1,4 |
| VIIi | 17,2–1,3 | 19,2–2,8 | 19,4–0,8 | 23,1–2,8 | 21,1–1,6 |
| VIIj | 17,9–0,3 | 18,6–1,4 | 18,7–0,3 | 23,5–2,1 | 21,3–0,5 |
| VIIk | 17,5–1,6 | 17,9–1,8 | 19,2–1,0 | 22,6–1,0 | 22,7–0,8 | n = 19 for control, n = 18 for ethanol. In all the rest cases n = 3.
*statistically reliable differences (in comparison with ethanol), p < 0,05.

TABLE 11

Relation of various functions of lipids in adipocytes after incubation of cells in the presence of compounds of aminoacridine series.
Symbols - see Table 9.

| Compound | FFA/TG | PL/TG | PL/CL |
|---|---|---|---|
| control | 0.94 | 0.67 | 0.73 |
| ethanol | 0.88+ | 0.61 | 0.70 |
| VIIe | 1.00 | 1.06 | 0.95* |
| VIj | 1.08 | 0.85 | 0.80 |
| Vp | 1.03 | 0.89 | 0.83* |
| VIId | 1.16* | 0.73 | 0.69 |
| Vaa | 0.94 | 0.58 | 0.63 |
| VIIj | 1.00 | 0.86 | 0.83 |
| VIIk | 0.93 | 0.58 | 0.61 |
| VIII | 1.00 | 0.78 | 0.75 |
| probucol | 1.10* | 0.69 | 0.84* | n = 19 for control and ethanol. In all the rest cases n = 3.
* - p < 0.05 in comparison with "ethanol" group.
+ - p < 0.05 in comparison with control.

TABLE 12

Relations of separate functions of lipids in incubation medium after incubation of adipocytes in the presence of aminoacridine derivatives.
Symbols - see Table 9.

| Compound | FFA/TG | PL/TG | PL/CL |
|---|---|---|---|
| control | 0.97 | 0.64 | 0.80 |
| ethanol | 0.99 | 0.68 | 0.81 |
| VIIe | 0.95 | 0.59 | 0.73 |
| VIj | 1.03 | 0.62 | 0.65 |
| Vp | 0.92 | 0.52 | 0.65 |
| VIId | 0.96 | 0.67 | 0.75 |
| Vaa | 0.92 | 0.55 | 0.71 |
| VIIj | 1.07 | 0.81 | 0.89 |
| VIIk | 1.10 | 0.84 | 0.96 |
| VIII | 1.00 | 0.77 | 0.91 |

TABLE 13

Distribution of separate lipids between cells and incubation medium after incubation of adipocytes in the presence of compounds of aminoacridine series.
Symbols - see Table 9. Index "c" - cells. index "m" - incubation medium.

| Compound | PLc/PLm | FFAc/FFAm |
|---|---|---|
| control | 1.01 | 0.96 |
| ethanol | 0.93 | 0.92 |
| VIIe | 1.44* | 0.84 |
| VIj | 1.24* | 0.95 |
| Vp | 1.41* | 0.93 |
| VIId | 0.97 | 1.07* |
| Vaa | 1.04 | 1.01 |
| VIIj | 1.08 | 0.93 |
| VIIk | 0.78 | 0.95 |
| VIII | 0.97 | 0.96 | n = 19 for control and ethanol.
In all the rest cases n = 3.
* - p < 0.05.

Compound Vo. This compound is analogous to VIIe according to the effect on lipid composition of adipocytes. Accumulation of phospholipids in a cell (Tables 9, 11, 13), enhanced ejection of triacylglycerides into external medium (Tables 10, 12) and sharp decreases in the content of methyl ester of fatty acids (Table 9) are observed.

Compound VIId. This compound has a significant lipolytic effect, which is proved by an increase of content of fatty acids in a cell (Table 9) and a sharp increase of FFA/TG relation in favor of fatty acids (Table 11).

The performed studies prove the fact, that the declared compounds have an effect on lipid cell composition. Compounds VIIe, Vo and VIId show the most potent effect. The other studied compounds also influence the lipid content. A combin&tion of the described properties of the three mentioned compounds permits consideration of them as the most promising from the point of view of the development of new drugs to treat diseases connected with lipid metabolism disorders. The compounds VIIe and Vo which increase PL/TG relations and decrease cell cholesterol level, may be recommended for the study as potential anti-atherosclerotic drugs and compounds to prevent adipose degeneration of organs. Compound VIId due to its significant lipolytic effect may be considered as a drug to treat diseases accompanied by obesity. Compounds Vp and VIId are not inferior of the most effective drug in world-wide clinical practice—probucol, and compound VIIe supresses it.

In summary, the proposed derivatives of 9-aminoacridine have a lower toxicity than known drugs (tacrine, amiridine) have antiamnestic activity, they are effective in comparative or lower doses ensuring a wider therapeutic range of activity of the given compounds. An additional valuable property of these compounds is lipid-regulative activity, which proves perspectiveness of mentioned compounds as anti-atherosclerotic drugs and drugs to treat diseases accompanied by lipid metabolism disorders, and in particular phospholipids (obesity, diabetes mellitus, and membronopathy of various genesis).

We claim:
1. Compounds of the formula

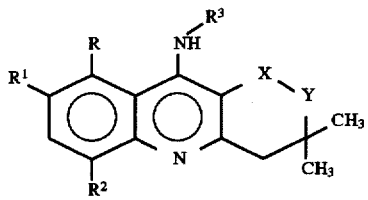

where R=H or $CH_3$;
$R^1$=H, $CH_3$ or Br;
$R^2$=H or $CH_3$;
$R^3$=$C_1$–$C_5$ alkyl, diethylaminoethyl, phenylmethyl, or substituted phenylmethyl wherein the substituents of the phenyl group are Cl or $CH_3$;
X=C=O or CHOH, Y=$CH_2$ or X+Y=CH=CH and their pharmaceutically acceptable acid addition salts, thereof showing psychotropic, antiamnestic and lipid-regulative activity.

* * * * *